United States Patent [19]

DeMarzo

[11] Patent Number: 5,031,629
[45] Date of Patent: Jul. 16, 1991

[54] HYPERTENSION ANALYZER APPARATUS

[76] Inventor: Arthur P. DeMarzo, 2S558 White Birch La., Wheaton, Ill. 60187

[21] Appl. No.: 360,992

[22] Filed: Jun. 2, 1989

[51] Int. Cl.$^5$ ............................................. A61B 5/02
[52] U.S. Cl. .................................. 128/670; 128/682; 128/680; 128/734
[58] Field of Search ............... 128/670, 734, 682, 683, 128/680, 695, 696, 706, 707, 709, 710, 713, 715, 720

[56] References Cited

U.S. PATENT DOCUMENTS

| | | | |
|---|---|---|---|
| 4,450,527 | 5/1984 | Sramek | 128/734 |
| 4,677,984 | 7/1987 | Sramek | 128/681 |
| 4,733,670 | 3/1988 | Hays et al. | 128/734 |
| 4,781,201 | 11/1988 | Wright et al. | 128/709 |
| 4,807,638 | 2/1989 | Sramek | 128/734 |
| 4,860,759 | 8/1989 | Kahn et al. | 128/706 |

Primary Examiner—Francis Jaworski
Assistant Examiner—George Manuel
Attorney, Agent, or Firm—Welsh & Katz, Ltd.

[57] ABSTRACT

The present invention is directed to an apparatus that is compact, portable and highly effective in performing a hemodynamic profile of a patient, and is particularly useful in generating such profiles for the purpose of diagnosing and treating hypertension. The apparatus includes noninvasive blood pressure and cardiac output monitors, computing means and the apparatus calculates a patient's cardiac index and systemic vascular resistance index for use in diagnosing hypertension.

15 Claims, 2 Drawing Sheets

HYPERTENSION ANALYZER APPARATUS

The present invention generally relates to apparatus for performing hemodynamic analysis on patients, and more specifically relates to a self-contained, compact, noninvasive apparatus for performing such hemodynamic analysis.

While much research is being conducted on hypertension, particularly with respect to the causation and treatment of the condition, it is generally believed that hypertension is caused by an increase in cardiac output of the patient or by a gradual increase in the systemic vascular resistance of the patient. The hemodynamic characteristics of a patient's system can be defined by the relationship between the systemic vascular resistance, the mean arterial pressure, and the cardiac output. It is generally known that the brain controls the arterial pressure in providing adequate perfusion of a patient, and increases the pressure if an increased systemic vascular resistance condition exists.

The most common diagnosis of hypertension through noninvasive procedures involves the measurement of systolic and diastolic arterial pressures and a comparison of those measured values with what are considered to be normal for patients of the same sex, age and known conditions.

Treatment of hypertension is now conducted utilizing three general classes of drugs which are diuretics, vasodilators and negative inotropes. Because of the significant number of variable conditions that can be diagnosed in hypertension patients, it is not uncommon to prescribe a combination of drugs for specific patients in order to provide the optimum treatment. While any single drug of the above-described classes of drugs can reduce the blood pressure when given in adequate dosage, the consequences of the type of drug can be significant, particularly in terms of the perfusion requirement of the body tissues of the patient. If inadequate perfusion of certain organs occurs, long term damage to those organs, and even patient death, can occur. Before these profound consequences are experienced, however, patients can develop side effects such as depression, dizziness, and male patients can also experience impotence.

There is currently no single diagnostic instrument that is commercially available for the assessment of hemodynamic factors associated with hypertension. Even though there are believed to be over 60 million Americans who suffer from hypertension, with the direct cost of hypertensive treatment estimated at $8 to $10 billion annually, the current mode of prescribing medication to treat hypertension is an imprecise science that is predominantly an empirical trial and error method of stepped care approach by physicians who make treatment decisions with insufficient information. Since many medications are becoming increasingly expensive, such trial and error methods need to be replaced by a scientific methodology of assessing the physiological parameters of the hypertension. If such a scientific methodology can be used to define the desired specific hemodynamic parameters, then an adequate program of treatment can be prescribed which reduces the undesirable side effects and also increases the cost efficiency through the reduction of wasted expensive medications.

It is therefore a primary object of the present invention to provide a single piece of equipment which is compact, portable and convenient to use, and which is adapted for use in a physician's office to noninvasively generate hemodynamic profiles of patients with hypertension. This data can then be used by the treating physician for prescribing treatment and for follow-up monitoring of the patient.

It is another object of the present invention to provide such an improved apparatus using commercially available medical electronic instrumentation and to process the data that is obtained with such instrumentation in such a way so as to provide brief, meaningful and accurate reports that can be used by a physician to prescribe the most appropriate medication for a patient having hypertension.

Yet another object of the present invention is to provide such an improved apparatus which utilizes a computing means which is provided with software for controlling the medical instrumentation and which utilizes formats, prompts and instructions that enable easy and effective measurement of various hemodynamic characteristics which results in fast and accurate reports that contain significantly useful data and indices that are most relevant to the proper prescription of medication.

Other objects and advantages will become apparent from the following detailed description, in conjunction with the attached drawing, in which:

Figures 1, 2, 3:
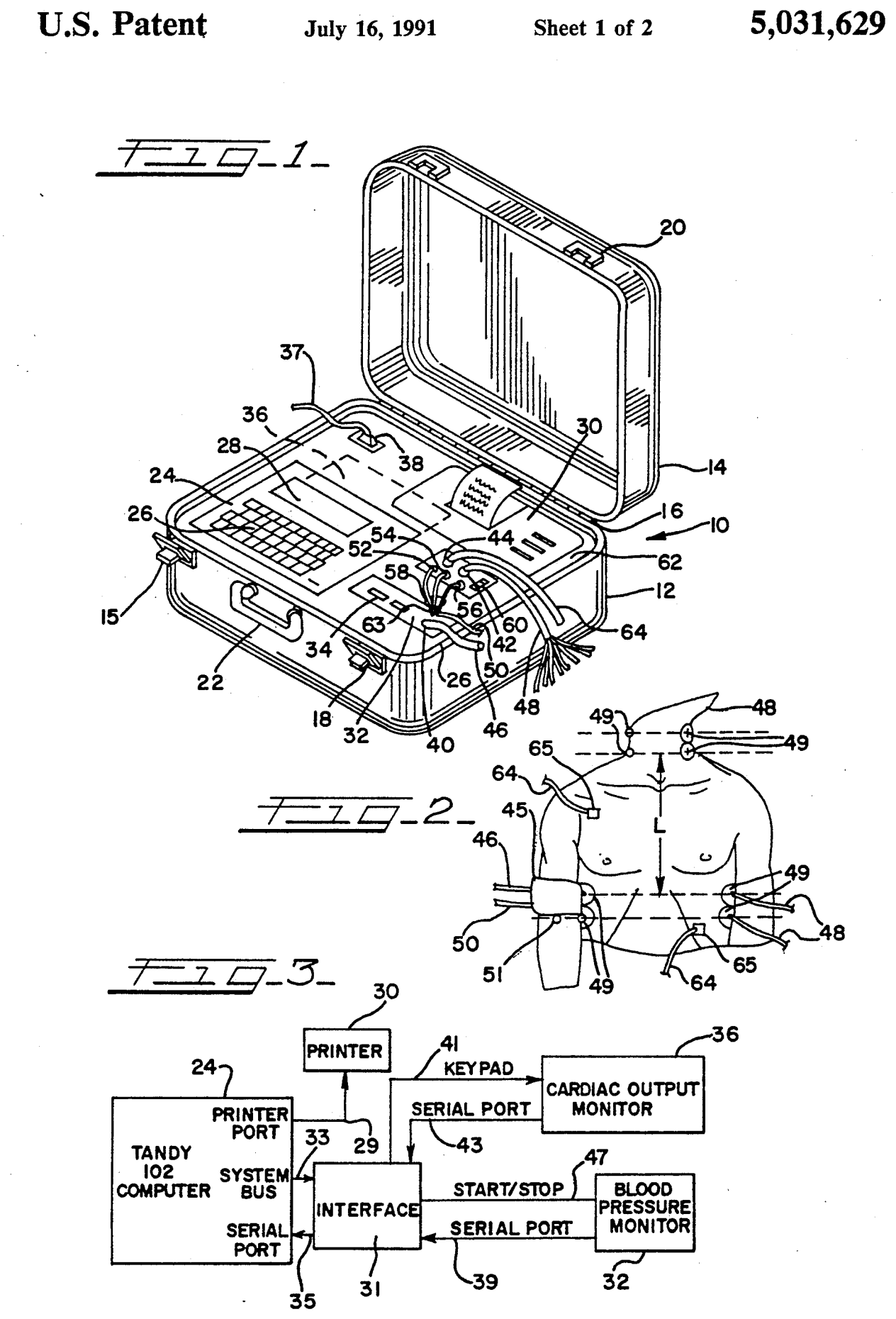

FIG. 1 is a perspective drawing of an apparatus embodying the present invention; and, FIG. 2 is an illustration of the proper placement of electrodes of a noninvasive cardiac output monitor and the attachment of a blood pressure cuff for the blood pressure monitor;

FIG. 3 is a schematic block diagram of the apparatus embodying the present invention; and, FIG. 4 is a flow chart of the software that is utilized in operating the system of the present invention.

DETAILED DESCRIPTION

Figure 4:
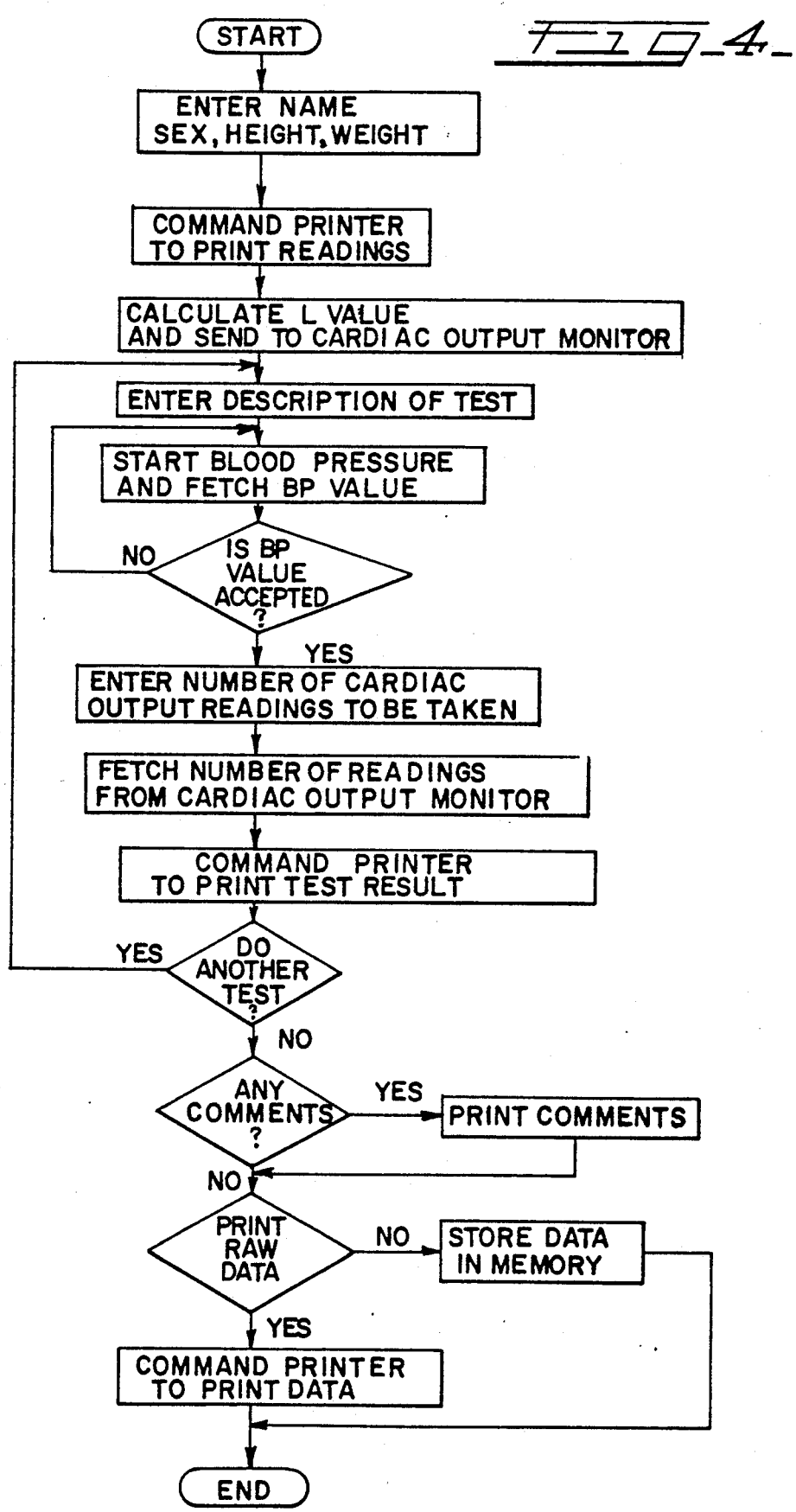

Broadly stated, the present invention is directed to an apparatus that is compact, portable and highly effective in performing a hemodynamic profile of a patient, and is particularly useful in generating such profiles for the purpose of diagnosing and treating hypertension. While there are many medications that are useful in treating hypertension, they generally can be characterized as negative inotropes which are believed to reduce the contractility of the heart itself, or vasodilators, which reduce the systemic vascular resistance of the arterial system. While the selection of the proper, most optimum medication has often been made on the basis of a more or less hit or miss methodology by many practicing physicians, it is generally recognized that the most appropriate medication can be prescribed if an adequate hemodynamic profile is available to the physician. Moreover, while there are many hemodynamic characteristics that can be used by a physician in prescribing the proper medication, it is generally recognized that some characteristics are much more relevant to such analysis than others. In this regard, blood pressure, heart rate, cardiac index and systemic vascular resistance index values are sufficient to enable a physician to prescribe the most appropriate medication for a hypertensive patient.

The present invention is directed to an apparatus that noninvasively measures blood pressure and cardiac output, and the apparatus includes a computing means, such as a small personal computer which utilizes the cardiac and blood pressure data to calculate the cardiac index and the systemic vascular resistance index and provides a printed report that includes this data in addition to blood pressure and heart rate data in easily readable form to the physician for his use in prescribing medication. The apparatus includes software which guides the physician or operator through the necessary steps in obtaining the data, and specifically provides appropriate prompts and instructions for guiding the physician through the diagnostic procedure. The apparatus conveniently provides an averaging function of various readings through different sets of tests that are taken with the patient in different positions and calculates the desired indices that are used in providing the printed report.

Of particular significance is the fact that the indices are a function of the surface area of the body of the patient and the apparatus is adapted to provide these indices utilizing easily obtained measurements of height and weight which are input into the personal computer for the patient being tested. The apparatus then calculates the indices using this data in conjunction with measured hemodynamic values that are obtained. Thus, the physical measurement of distances between properly placed electrodes on the body of a patient which are often done in conjunction with obtaining noninvasive cardiac output values is unnecessary. The present invention is therefore much more convenient and easy to use in this regard.

Turning now to the drawings, and particularly FIG. 1, apparatus, indicated generally at 10, is illustrated and includes a case having a base portion 12, a cover portion 14 that is preferably connected to the base portion by a hinge mechanism 16 and two latching mechanisms 18 that interconnect with a keeper 20 for latching the cover portion to the base portion 12. A handle 22 is provided for carrying the portable apparatus. The compactness of the system is such that the outer dimensions of the case are only approximately 17 inches by 21 inches by 7 inches with the cover portion closed. The apparatus also includes a computing means 24, preferably a Tandy Model 102 computer having a 32k memory (not shown), a keyboard 26 and an LCD display 28. An associated thermal printer 30, preferably a Model DPU-411 printer manufactured by Seiko Instruments, Inc., is provided for printing the previously described reports. A commercially available blood pressure monitor 32 has an associated display 34 and this display indicates various aspects of the heart function. This display illustrates the letter "R" for heart rate and the letter "K" for Korotkoff sound. After it has identified the pulse and has displayed the above indications, it numerically displays the blood pressure, and the computing means display also displays the same value. A sound generating means (not shown) is located within the base portion 12 and it provides a beeping sound, indicating heart rate. Beneath the computing means 24 is a cardiac output monitor 36, which is a commercially available monitor unit. The system is powered by an A.C. source which is connected to the unit by a cord 37 via connector 38. The cardiac output monitor is preferably a Model NCCOM3 monitor manufactured by Bomed Manufacturing, Ltd. of Irvine, CA and the blood pressure monitor is preferably an Accutracker monitor, Part No. 1Q3AMUK, manufactured by Suntech Medical Instruments, Inc. The monitors 32 and 36 are interconnected with the computing means 24 and also have leads extending to connectors 40, 42 and 44. A blood pressure cuff 45 (see FIG. 2) is connected to the connector 40 of the blood pressure monitor via line 46 and a multi-conductor cable 48 connects to connector 42 and to electrodes 49 for the cardiac output monitor. The cable 48 comprises a number of individual conductors that extend to individual electrodes 49 attached as shown in FIG. 2. A cable 64 connects to connector 44 and also extends to electrodes 65 as shown in FIG. 2 that are preferably positioned on the patient for monitoring what is commonly referred to as the Lead II ECG signal.

The blood pressure monitor is of the auscultatory type which has a microphone associated with it and requires an ECG signal. The ECG signal is available from the cardiac output monitor for use by the blood pressure monitor. In this regard, the ECG+, ECG− and ground signals are present at snap connectors 52, 54 and 56, respectively. These signals are input to the blood pressure monitor via leads 58 which have cooperative snap connectors for connecting to the snap connectors 52, 54 and 56. A cable 50 connects to connector 63 and also extends to a microphone 51 that is preferably placed over the brachial artery and provides the means for detecting the Korotkoff sound when the pressure is reduced in the cuff so as to permit flow through the artery. The cardiac output monitor also has a switch 60 for turning a beeper on and off, the beeper providing a beeping sound when the pulse is detected. The blood pressure monitor also displays an indication on its display 34 for each occurrence of a heart beat. An operator can listen to the beep from the cardiac output monitor while observing the visual indication and thereby gain a greater degree of confidence that the system is operating properly when coincidence of these visual and audio indications exist. While the cardiac output monitor 36 is preferably secured to the bottom of the compartment 12, the computing means 24 is preferably mounted above the cardiac output monitor and is preferably attached to an upper face plate 62 to which the connectors 38, 40, 42, 44 and 63 are also attached, as is the printer 30. The blood pressure monitor is preferably mounted to the face plate alongside the computing means 24, and an opening of approximately 7 inches by 1½ inches is cut in the face plate so that an operator can observe the display 34 of the blood pressure monitor.

As illustrated in the block diagram of FIG. 3, the computing means 24 is connected to the printer 30 via a cable 29 from a printer port. The computing means main bus is connected to an interface 31 via lines 33 and the serial port of the computing means 24 is also connected to the interface via an RS232 interconnection 35. The interface is also connected to the monitors 32 and 36 via RS232 interconnections 43 and 39, respectively. A cable 41 is also provided between the interface 31 and the cardiac output monitor using the keyboard of the computing means 24. In this manner, the monitor 36 can be located beneath the computing means 24 out of view, and yet can be operated in a normal manner. A start/stop command line 47 is provided between the interface and the blood pressure monitor for controlling the operation of the same. The interface is preferably a printed circuit board having bidirectional gating elements for selectively controlling the operation of one or the other of the two monitors 32 or 36. The system bus connections provide the controlling signals for activating the gating elements in the manner that is well known in the electrical arts.

As previously described, the computer has an associated memory in which instructions are programmed for operating the apparatus to accomplish the functionality that has previously been described. In the preferred embodiment, the keyboard 26 is used to provide input data concerning the patient which is used in connection with the running of the tests which result in the hemodynamic profiles being generated. As shown in the following example, the entirety of the report is illustrated and includes the caption "Hypertension Analysis", the patient name, the date the tests were performed as well as the weight, height and then the test results are printed out for various positions including supine, sitting, standing and hyperventilated while standing state. The tests are run in each of these four positions or stress levels and yield the blood pressure values, heart rate values, cardiac index values, and the systemic vascular resistance index values.

| HYPERTENSION ANALYSIS | | | | |
|---|---|---|---|---|
| PATIENT NAME: JOHN DOE 02/11/89 WEIGHT = 180 LBS HEIGHT = 72 INCHES | | | | |
| TEST MODE | BP | HR | CI | SVRI |
| SUPINE | 140/080 | 88 | 2.4 | 41 |
| SITTING | 150/090 | 88 | 2.4 | 45 |
| STANDING | 150/080 | 88 | 2.4 | 43 |
| HYPERVENT | 140/080 | 88 | 2.4 | 41 |

During the running of the tests, the first prompt provided on the computer display requests that the operator enter the patient's name and sex. After this is done, the patient's weight in pounds is requested, as well as the height in inches. The machine is then placed in test mode by an input command and the operator is requested to provide the number of sets of readings that are to be used, which can be programmed between virtually any limits, but typically between 1 and 10, and preferably 4. In this regard, it should be understood that the cardiac output monitor operates to measure the cardiac functions over the span of 12 heart beats, and then issues a signal that is the average of the cardiac output for those 12 heart beats. The computing means receives this data and it then performs its own averaging of these cardiac output values based upon the programmed number of sets that the operator has specified. The sets of measurements are taken with the patient in each of several positions, including the supine position, sitting position and standing position. Also a set of measurements are taken when the patient is in a hyperventilated condition. After these readings are taken over a period of approximately 20 minutes, the computing means calculates the indices and prints out the above report which provides the averaged values of the blood pressure, heart rate, cardiac index and systemic vascular resistance index.

To obtain the cardiac index, the cardiac output which is measured by the noninvasive cardiac output monitor is divided by the surface area of the body, which is calculated from the height and weight. The cardiac output is the volume of blood which the heart pumps in one minute and is an important cardiovascular parameter. The cardiac output is the volume of blood that is pumped per stroke (generally referred to as the stroke volume or SV) multiplied by the number of strokes or the heart rate of the patient. It is generally accepted that the Kubicek et al. study described an improved equation for the calculation of stroke volume, as described in the article "The Minnesota Impedance Cardiography-Theory And Applications", Biochem. Eng. 9:410 (1974). The cardiac output monitor measures the electrical impedance change utilizing the equation $$SV = \frac{RL^2}{Z_0^2} \times T(\Delta Z/\text{sec})$$

where SV equals stroke volume, R is the specific resistivity of blood, L is the distance between sensing electrodes, $Z_o$ is the base electrical impedance, T is the ventricular ejection time and $\Delta Z/\text{sec}$ is the maximum rate of impedance change. The L factor in the above equation requires measurement of the distance between sensing electrodes which obviously varies among patients being tested. The L factor requires that the electrodes be properly placed and measured. Assuming that the electrodes are properly placed, there is a direct relationship between height and weight and the distance between the properly placed electrodes, so that the L factor can be calculated or converted from height and weight measurements with a high degree of accuracy.

In accordance with an important aspect of the present invention, the apparatus utilizes a database in the computing means memory for converting the height and weight data to an L factor for use in calculating the stroke volume according to Kubicek's equation. The cardiac output is obtained by multiplying the stroke volume by the heart rate, and the cardiac output is then divided by the surface area of the body to result in the cardiac index figure or value. In a similar manner, the systemic vascular resistance index can be calculated from the cardiac index and the mean arterial pressure. The blood pressure values that are obtained during the testing process are divided by the cardiac index value to obtain the systemic vascular resistance index. The mean arterial pressure as utilized in this equation is the generally accepted diastolic pressure plus one-third of the difference between the systolic and diastolic pressure.

The apparatus of the present invention is extremely easy to use in that it utilizes a commercially available noninvasive blood pressure monitor and a commercially available noninvasive cardiac output monitor, uses the data from these monitors and automatically calculates the cardiac index and systemic vascular resistance index using the height and weight information of the patient together with the heart rate and blood pressure values that are obtained during the testing procedure. The report that is then printed by the apparatus provides these four values which are all of the values that are really necessary to determine the most appropriate medicinal treatment for hypertension.

In this regard, the values that are provided in the report are extremely useful for a medical practitioner to prescribe the most appropriate medication for a patient having hypertension. It is generally acknowledged that a patient having a cardiac index value obtained while in a resting supine position is considered normal if it is within the range of approximately 2.8 to 4.2, and that a value in excess of 4.2 would suggest that a negative inotrope type of medication would be appropriate to prescribe. Similarly, a systemic vascular resistance index value obtained from the patient in the same resting supine position is generally considered normal if it is within the range of approximately 20 to 30, and that a value in excess of 30 would suggest that it may be appropriate to prescribe a vasodilator type of medication.

If the values of both indices are above the upper end of their respective ranges of normalcy, then a combination of both types of drugs may be appropriate.

While various embodiments of the present invention have been shown and described, it should be understood that various alternatives, substitutions and equivalents can be used, and the present invention should only be limited by the claims and equivalents thereof.

Various features of the present invention are set forth in the following claims.

What is claimed is:

1. A self-contained compact, portable apparatus for noninvasively performing a hemodynamic profile of a patient, and particularly adapted for use in diagnosing hypertension, the apparatus comprising, in combination:

means for noninvasively monitoring and measuring thoracic impedance of the patient, and for generating electrical signals that are indicative of the measured thoracic impedance of the patient;

means for noninvasively monitoring and measuring the blood pressure of the patient, and for generating electrical signals that are indicative of the measured blood pressure levels of the patient;

detachable cuff means for application to the patient, said cuff means being adapted to be connected to said blood pressure monitoring and measuring means for providing blood pressure measurements of the patient thereto;

means for noninvasively monitoring and measuring the electrocardiological profile of the patient and for generating electrical signals that are indicative of the measured electro-cardiological profile of the patient;

detachable electrode means adapted to be connected to the patient and to the electrocardiological profile monitoring and measuring means for providing input signals thereof;

computing means operatively connected to each of said monitoring and measuring means and adapted to receive and process the electrical signals generated by each of said monitoring and measuring means, said computing means including printing means the printing reports of hemodynamic data, display means for displaying information relating to operation of the apparatus, and keyboard means for entering data concerning a patient and for controlling the operation of the apparatus; and compact portable container means including mounting means located within the container means for housing each of said monitoring and measuring means and said computing means;

said computing means receiving said electrical signals from each of said monitoring and measuring means and generating a visual display on said display means that includes a plurality of hemodynamic indices and measurements including value for blood pressure, chart rate, cardiac index and systemic vascular resistance index of the patient being monitored, and also generating a written report of said values.

2. Apparatus as defined in claim 1 wherein the height and weight of the patient is entered on the keyboard means, said computing means being adapted to process the electrical signals generated from each of said monitoring and measuring means and produce said visual display and written report in relation to the height and weight of the patient being monitored.

3. Apparatus as defined in claim 2 wherein said computing means generates said values based upon an average of a predetermined number of measurement taken over a short period of time.

4. Apparatus as defined in claim 1 wherein said container means comprises a generally rectangular cross-sectional base portion having a cooperatively fitting cover portion that is adapted to open relative to the base portion, said base portion having sufficient depth to receive said computing means, and each of said monitoring and measuring means, said container means having a carrying handle and locking means for releasably locking said cover portion to said base portion.

5. APparatus as defined in claim 4 wherein the outside walls of said base portion and cover portion are fabricated of a substantially rigid material.

6. Apparatus as defined in claim 1 wherein said computing means includes a data base for correlating height and weight values of a patient to a value of L indicating the distance on a patient between properly placed electrodes of a cardiac monitoring means, for use in calculating the stroke volume in the equation:

$$SV = r \times (L/Z_0)^2 \times T \times dZ/dt$$

where
   r is the resistivity of blood in ohm-cm
   L is the distance between the sensing electrodes in cm
   $Z_0$ is the basal impedance of the thorax in ohms
   T is the ejection time in seconds, and
   dZ/dt is the first derivative of the impedance change ($\Delta Z$) in the thorax during $\Delta$ejection time T.

7. Apparatus as defined in claim 1 wherein said thoracic impedance monitoring and measuring means is of the type which measures diathoracic impedance for a predetermined number of heart beats and generates an electric signal indicating the average value of said thoracic impedance for said predetermined number of heart beats, said computing means being adapted to select and receive a predetermined number of said electric signals and generate an average value of the same.

8. Apparatus as defined in claim 7 wherein said predetermined number of heart beats is 9 and said predetermined number of said electric signals is within the range of 1 to 10.

9. A self-contained compact, portable apparatus for noninvasively performing a hemodynamic profile of a patient, and particularly adapted for use in diagnosing hypertension, the apparatus comprising:

means for noninvasively monitoring and measuring thoracic impedance of the patient, and for generating electrical signals that are indicative of the measured thoracic impedance of the patient;

means for noninvasively monitoring and measuring the blood pressure of the patient, and for generating electrical signals that are indicative of the measured blood pressure levels of the patient;

detachable cuff means for application to the patient, said cuff means being adapted to be connected to said blood pressure monitoring and measuring means for providing blood pressure measurements of the patient thereto;

means for noninvasively monitoring and measuring the electrocardiological profile of the patient and for generating electrical signals that are indicative of the measured electrocardiological profile of the patient;

detachable electrode means adapted to be connected to the patient and to the electrocardiological profile monitoring and measuring means for providing input signals thereto;

computing means operatively connected to each of said monitoring and measuring means and adapted to receive and process the electrical signals generated by each of said monitoring and measuring means, said computing means including printing means for printing reports of hemodynamic data, display means for displaying information relating to the operation of the apparatus, and keyboard means for entering data concerning a patient, including the height and weight of the patient, said keyboard also being adapted to control the operation of the apparatus; and compact portable container means having a rectangular base portion and a cover portion operable between an open position exposing the interior of said base portion and a closed position covering said base portion, said base portion including mounting means located therein for housing each of said monitoring and measuring means and said computing means;

said computing means receiving said electrical signals from each of said monitoring and measuring means and generating a plurality of hemodynamic indices and measurements including blood pressure, heart rate, cardiac index and systemic vascular resistance index of the patient being monitored.

10. Apparatus as defined in claim 9 wherein said computing means includes a data base for correlating height and weight values of a patient to a value of L indicating the distance on a patient between properly placed electrodes of a cardiac monitoring means, for use in calculating the stroke volume in the equation:

$$SV = r \times (L/Z_0)^2 \times T \times dZ/dt$$

where
 r is the resistivity of blood in ohm-cm
 L is the distance between the sensing electrodes in cm
 $Z_0$ is the basal impedance of the thorax in ohms
 T is the ejection time in seconds, and
 dZ/dt is the first derivative of the impedance change ($\Delta Z$) in the thorax during ejection time T.

11. Apparatus as defined in claim 9 said computing means in operative to generate a printed report that includes values for blood pressure, heart rate, cardiac index and systemic vascular resistance index of the patient being monitored.

12. Apparatus as defined in claim 11 wherein said printed report provided by said apparatus is sufficient to enable a medical practitioner to effectively prescribe the most appropriate combination of hypertension medication, a value of cardiac index above a predetermined value indicating that a negative inotrope type of medication should be most eficacious, a value of systemic vascular resistance index above a predetermined value indicating that a vasodilator type of medication should be most efficacious.

13. Apparatus as defined in claim 9 wherein said computing means generates a visual display on said display means that includes values for blood pressure, heart rate, cardiac index and systemic vascular resistance index of the patient being monitored.

14. Apparatus as defined in claim 9 wherein said blood pressure monitoring and measuring means is of the auscultatory type which requires an ECG input signal for its operation, said blood pressure monitoring and measuring means having a microphone adapted to be applied to the brachial artery of the patient, said microphone being connected thereto for providing said ECG input signals, the apparatus having leads interconnecting said blood pressure monitoring and measuring means to said thoracic impedance monitoring and measuring means for providing said ECG input signals thereto.

15. Apparatus as defined in claim 9 wherein manipulation of said keyboard means of said computing means is effective to initiate operation of each of said monitoring and measuring means during operation of said apparatus.

* * * * *

UNITED STATES PATENT AND TRADEMARK OFFICE
CERTIFICATE OF CORRECTION

PATENT NO. : 5,031,629
DATED : July 16, 1991
INVENTOR(S) : Arthur P. DeMarzo It is certified that error appears in the above-identified patent and that said Letters Patent is hereby corrected as shown below:

```
Column 7, line 38, change "thereof" to --thereto--.
Column 7, line 57, change "value" to --values--.
Column 7, line 58, change "chart" to --heart--.
Column 8, line 3, change "measurement" to --measurements--.
Column 8, line 32, change "Δejection" to --ejection--.
Column 8, line 43, change "9" to --12--.
Column 10, line 5, after "9" insert --wherein--.
Column 10, line 16, change "eficacious" to --efficacious--.
```

Signed and Sealed this

Twenty-second Day of December, 1992

*Attest:*

DOUGLAS B. COMER

*Attesting Officer*         Acting Commissioner of Patents and Trademarks